United States Patent
Damrau et al.

(10) Patent No.: US 7,358,381 B2
(45) Date of Patent: Apr. 15, 2008

(54) RACEMOSELECTIVE PREPARATION OF BRIDGED METALLOCENE COMPLEXES HAVING UNSUBSTITUTED OR 2-SUBSTITUTED INDENYL LIGANDS

(75) Inventors: Hans-Robert-Hellmuth Damrau, Constance (DE); Patrik Müller, Frankfurt (DE); Valerie Garcia, Compiègne (FR); Christian Sidot, Compiègne (FR); Christian Tellier, Compiègne (FR); Jean-François Lelong, Tracy-le-Mont (FR); Eric Huriez, Selens (FR)

(73) Assignee: Basell Polyolefine GmbH, Wesseling (DE)

( * ) Notice: Subject to any disclaimer, the term of this patent is extended or adjusted under 35 U.S.C. 154(b) by 378 days.

(21) Appl. No.: 10/532,522

(22) PCT Filed: Oct. 22, 2003

(86) PCT No.: PCT/EP03/11678

§ 371 (c)(1),
(2), (4) Date: Jun. 24, 2005

(87) PCT Pub. No.: WO2004/037834

PCT Pub. Date: May 6, 2004

(65) Prior Publication Data

US 2006/0111527 A1 May 25, 2006

Related U.S. Application Data

(60) Provisional application No. 60/431,807, filed on Dec. 9, 2002.

(30) Foreign Application Priority Data

Oct. 25, 2002 (DE) ................ 102 50 062

(51) Int. Cl.
 *C07F 17/00* (2006.01)
 *B01J 31/00* (2006.01)
 *C08F 4/44* (2006.01)

(52) U.S. Cl. .................. 556/53; 556/43; 556/54; 556/58; 548/402; 502/103; 502/117; 526/160; 526/170; 526/943

(58) Field of Classification Search .................. 556/43, 556/53, 54, 58; 502/103, 117; 548/402; 526/160, 170, 943

See application file for complete search history.

(56) References Cited

U.S. PATENT DOCUMENTS 6,262,286 B1    7/2001  Gregorius et al.
6,323,149 B1 *  11/2001 Takemori et al. ........... 502/114
6,444,833 B1 *  9/2002  Ewen et al. .................... 556/11
2004/0010157 A1  1/2004  Damrau et al.
2006/0154804 A1 * 7/2006  Schottek et al. ............. 502/103

FOREIGN PATENT DOCUMENTS

| DE | 100 30 638 | 1/2002 |
| EP | 07-00935 | 3/1995 |
| EP | 0 997 480 | 5/2000 |
| EP | 1 275 662 | 1/2003 |
| WO | WO-92/09545 | 6/1992 |
| WO | WO-99/15538 | 4/1999 |
| WO | WO-02/00672 | 1/2002 |
| WO | WO-02/051878 | 7/2002 |

OTHER PUBLICATIONS

Waymouth, R. et al., "Enantioselective Hydrogenation of Olefins with Homogeneous Ziegler-Natta Catalysts", J. Am. Chem. Soc. (1990), vol. 112, pp. 4911-4914.
Waymouth, R. et al., "Enantioselective Cyclopolymerization: Optically Active Poly(methylene-1,3-cyclopentane)", J. Am. Chem. Soc. (1991), vol. 113, pp. 6270-6271.
Bochmann, M. et al., "Base-Free Cationic Zirconium Benzyl Complexes as Highly Active Polymerization Catalysts", Organometallics (1993), vol. 12, pp. 633-640.
Rheingold, A. et al., "Preparation and Properties of Chiral Titanocene and Zirconocene Dichloride Complexes of a Chiral Ligand", Organometallics (1992), vol. 11, pp. 1869-1876.
Wartchow, R. et al., "Synthesis and Characterization of rac-[ethylene-1,2-bis($n^5$-4,5,6,7-tetrahydro-1-indenyl)]zirconium bisamides (EBTHI)Zr(NHR)$_2$", Journal of Organometallic Chemistry, (1998) vol. 566, pp. 287-291.
Kaminsky W. et al Asymmetric oligomerization of propene and 1-butene with a zirconocene-aluminoxane catalyst. Agnew. Chem 101 (1989) Nr. 9 pp. 1304-1306.

* cited by examiner

*Primary Examiner*—Porfirio Nazario-Gonzalez
(74) *Attorney, Agent, or Firm*—Jarrod N Raphael; William R Reid

(57) ABSTRACT

The invention relates to a process for preparing racemic metallocene complexes by reacting transition metal complexes with cyclopentadienyl derivatives of alkali metals or alkaline earth metals and heating the reaction mixture obtained in this way to a temperature in the range from −78 to 250° C., to the corresponding metallocene complexes themselves and to their use as catalysts or as constituents of catalysts for the polymerization of olefinically unsaturated compounds or as reagents or catalysts in stereoselective synthesis.

28 Claims, No Drawings

RACEMOSELECTIVE PREPARATION OF BRIDGED METALLOCENE COMPLEXES HAVING UNSUBSTITUTED OR 2-SUBSTITUTED INDENYL LIGANDS

RELATED APPLICATIONS

This application is a national stage application (under 35 U.S.C. 371) of PCT/EP2003/011678 which claims benefit to German application 102 50 062.2 filed Oct. 25, 2002 and U.S. provisional application 60/431,807 filed Dec. 9, 2002.

The present invention relates to a process for preparing racemic metallocene complexes of the formula (I)

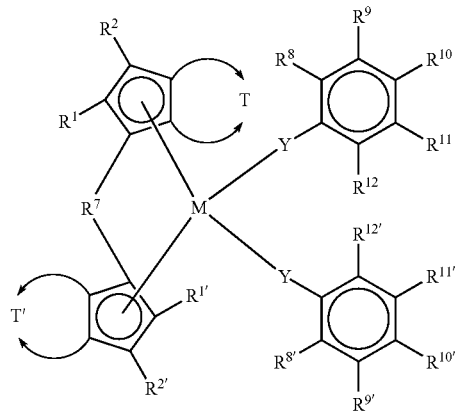

where

is a divalent group such as

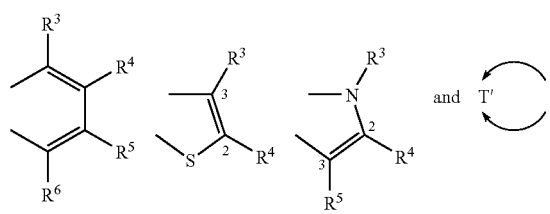

is a divalent group such as

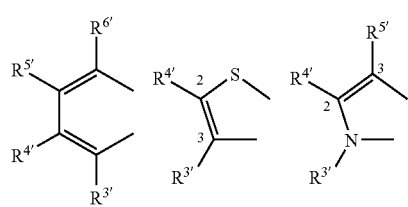

and the substituents and indices have the following meanings:

M is titanium, zirconium, hafnium, vanadium, niobium, tantalum, chromium, molybdenum, tungsten or an element of transition group III of the Periodic Table and the lanthanides, $R^1$, $R^2$, $R^3$, $R^4$, $R^5$, $R^6$, $R^9$, $R^{10}$, $R^{11}$, $R^{1'}$, $R^{2'}$, $R^{3'}$, $R^{4'}$, $R^{5'}$, $R^{6'}$, $R^{9'}$, $R^{10'}$, $R^{11'}$ are identical or different and are each hydrogen, halogen, $C_1$-$C_{20}$-alkyl, 3- to 8-membered cycloalkyl which may in turn bear a $C_1$-$C_{10}$-alkyl group as substituent $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, —$OR^{13}$, —$SR^{13}$, —$N(R^{13})_2$, —$P(R^{13})_2$, or $Si(R^{13})_3$, where $R^{13}$ are identical or different and are each $C_1$-$C_{10}$-alkyl, $C_6$-$C_{15}$-aryl, $C_3$-$C_{10}$-cycloalkyl, alkylaryl, where the radicals mentioned may be partially or fully substituted by heteroatoms, $R^8$, $R^{12}$, $R^{8'}$, $R^{12'}$ are identical or different and are each $C_1$-$C_{10}$-alkyl;

Y are identical or different and are each

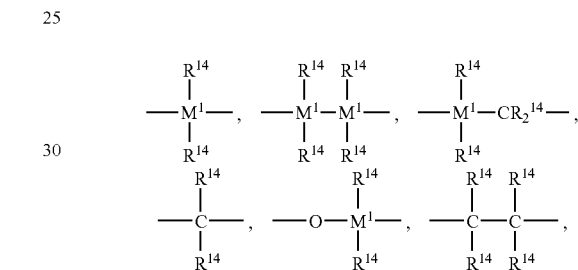

=$BR^{14}$, =$AlR^{14}$, —Ge—, —Sn—, —O—, —S—, =SO, =$SO_2$, =$NR^{14}$, =CO, =$PR^{14}$ or =$P(O)R^{14}$, where $R^{14}$ are identical or different and are each hydrogen, halogen, $C_1$-$C_{10}$-alkyl, $C_1$-$C_{10}$-fluoroalkyl, $C_6$-$C_{10}$-fluoroaryl, $C_6$-$C_{10}$-aryl, $C_1$-$C_{10}$alkoxy, $C_2$-$C_{10}$-alkenyl, $C_7$-$C_{40}$-arylalkyl, $C_8$-$C_{40}$-arylalkenyl, $C_7$-$C_{40}$-alkylaryl or two radicals $R^{14}$ together with the atoms connecting them form a ring, and $M^1$ is silicon, germanium or tin, $R^7$ is a -$[Z(R^{15})(R^{16})]_m$— group, where Z can be identical or different and are each silicon, germanium, tin or carbon, $R^{15}$, $R^{16}$ are each hydrogen, $C_1$-$C_{10}$-alkyl, $C_3$-$C_{10}$-cycloalkyl or $C_6$-$C_{15}$-aryl, m is 1, 2, 3 or 4, by reacting a transition metal complex of the formula (II)

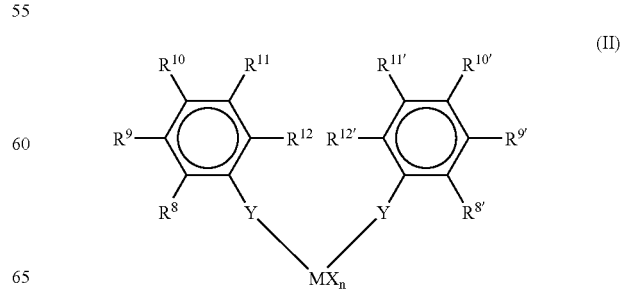

where

X are identical or different and are each hydrogen, halogen, $C_1$-$C_{10}$-alkyl, $C_6$-$C_{15}$-aryl, alkylaryl having from 1 to 10 carbon atoms in the alkyl part and from 6 to 20 carbon atoms in the aryl part, —$OR^{17}$ or —$NR^{17}_2$, where $R^{17}$ are identical or different and are each $C_1$-$C_{10}$-alkyl, $C_6$-$C_{15}$-aryl, $C_3$-$C_{10}$-cycloalkyl, alkylaryl, n is an integer from 1 to 4 and corresponds to the valence of M minus 2, with cyclopentadienyl derivatives of the formula (III)

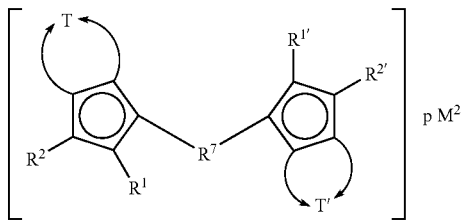

where $M^2$ is an alkali metal ion or alkaline earth metal ion, and p is 1 when $M^2$ is an alkaline earth metal ion and is 2 when $M^2$ is an alkali metal ion, and heating the resulting reaction mixture to a temperature in the range from −78 to +250° C.

The present invention further relates to corresponding racemic metallocene complexes of the formula (I) and to the use of racemic metallocene complexes of the formula (I) as catalysts or as constituents of catalysts for the polymerization of olefinically unsaturated compounds or as reagents or catalysts in stereoselective synthesis.

Apart from stereospecific olefin polymerization, enantioselective organic synthesis increasingly offers interesting possible uses for chiral metallocene complexes of metals of transition groups III-VI of the Periodic Table of the Elements. An example which may be mentioned is the enantioselective hydrogenation of prochiral substrates, for example prochiral olefins, as described in R. Waymouth, P. Pino, J. Am. Chem. Soc. 112 (1990), p. 4911-4914, or prochiral ketones, imines and oximes, as described in WO 92/9545. Further examples are the preparation of optically active alkenes by enantioselective oligomerization, as described in W. Kaminsky et al., Angew. Chem. 101 (1989), p. 1304-1306, and the enantioselective cyclopolymerization of 1,5-hexadiene, as described in R. Waymouth, G. Coates, J. Am. Chem. Soc. 113 (1991), p. 6270-6271.

The applications mentioned generally require the use of a metallocene complex in its racemic form, i.e. without meso compounds. In the case of the diastereomer mixture (rac and meso form) obtained in the metallocene synthesis of the prior art, the meso form firstly has to be separated off. Since the meso form has to be discarded, the yield of racemic metallocene complex is low.

There have therefore been attempts in the past to develop racemoselectve syntheses of ansa-metallocenes. A significant step in racemoselective syntheses of ansa-metallocenes proceeds via the intermediate of an ansa-metallocene bisphenoxide or an ansa-metallocene biphenoxide. Corresponding general synthesis routes are described, for example, in WO 99/15538 and in DE 10030638.

Despite the progress achieved, a generally applicable reaction scheme for the racemoselective synthesis of ansa-metallocenes has not yet been found. In the synthetic route via the ansa-metallocene bisphenoxide intermediate, the racemoselectivity of the synthesis is often dependent on the substitution pattern of the bisindenyl ligands used. Thus, usually only derivatives substituted in the 2 position of the bridged bisindenyl ligand can be converted racemoselectvely into the corresponding ansa-metallocene bisphenoxide intermediates. Without being tied to a particular theory, it is assumed that the reaction path possibly proceeds via a kinetically controlled mechanism in which two different diastereomeric transition states having a different energy are formed, so that the two isomers, namely the meso form and the racemate form, are formed in different amounts.

In all the synthetic routes via the corresponding ansa-metallocene bisphenoxide intermediates, the bisphenoxide complexes are thermally stable as soon as they are formed, so that no isomerization between rac and meso form occurs during the elimination of the phenoxide auxiliary ligands.

A disadvantage of the known syntheses using the multiply alkyl-substituted bi(s)phenoxide auxiliary ligands customarily employed is the relatively high solubility of these usually nonpolar complexes in the aromatic solvents customarily employed, which makes isolation of the complex in pure form by crystallization considerably more difficult.

It is an object of the present invention to overcome the disadvantages of the prior art and to find a process for the selective preparation of racemic metallocene complexes which are virtually free of the meso isomer (NMR measurement accuracy). In particular, it is an object of the present invention to find a racemoselective process for synthesizing metallocene complexes which leads in a simple and cost effective manner to end products which can be isolated in pure form. A further object is to find racemic metallocene complexes which can either be used directly as or in catalysts, primarily for olefin polymerization, or can after modification, for example after replacement of an "auxiliary ligand", be used as or in catalysts, primarily for olefin polymerization, or can be used as reagents or catalysts in stereoselectve synthesis.

We have found that this object is achieved by the process defined in the claims, by the racemic metallocene complexes (I) resulting therefrom and by their use as catalysts or in catalysts for the polymerization of olefinically unsaturated compounds or as reagents or catalysts in stereoselective synthesis.

It has surprisingly been found that the racemoselectve synthesis of metallocene complexes can be successfully carried out when phenoxide ligands and analogous derivatives which are alkyl-substituted in the 2,6 positions of the aromatic ring are used. The synthesis proceeds with high rac:meso ratios even with simple methyl substituents in the 2,6 positions. A particularly advantageous aspect of the preparative method of the present invention is that the solubility of the metallocene complexes can be significantly altered by introduction of, for example, polar substituents in the 4 position of the phenoxide ligand (or its analog), so that isolation of the complexes can be carried out in a simpler fashion and in higher yield.

Furthermore, it has been found that the process of the present invention can be carried out in a "single-vessel process" starting from the cyclopentadiene derivatives without isolation of intermediates and the process proceeds racemoselectively with high total yields under these conditions. For this reason, particular preference is given to carrying out the process of the present invention starting from the cyclopentadiene derivatives without isolation of intermediates after the individual process steps.

The terms "meso form", "racemate" and thus also "enantiomers" in the context of metallocene complexes are known and are defined, for example, in Rheingold et al., Organometallics 11 (1992), p. 1869-1876.

For the purposes of the present invention, the term "virtually meso-free" means that more than 80%, preferably at least 90%, of a compound are present in the form of the racemate, particularly preferably at least 95%.

For the purposes of the present invention, phenoxides (or their analogous derivatives) encompass all phenoxide ligands claimed according to the present invention and their analogous derivatives in which the phenol oxygen is replaced by other elements or groups as defined for Y.

It has surprisingly been found that metallocene bisphenoxide complexes having simple alkyl substituents in the 2 and 6 positions of the phenoxide ligand lead in high rac excesses to products which can be isolated and crystallized significantly more easily regardless of whether the customarily used bisindenyl ligand or its derivative are substituted in the 2 position of the indenyl.

The bridged transition metal complexes used as starting materials in the process of the present invention have the formula (II)

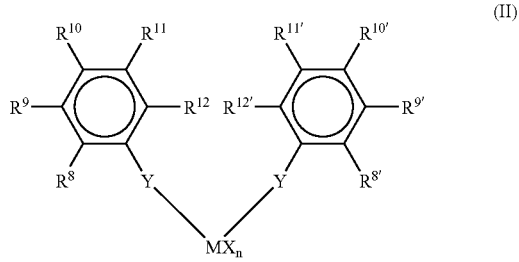

where

M is titanium, zirconium, hafnium, vanadium, niobium, tantalum, chromium, molybdenum, tungsten or an element of transition group III of the Periodic Table and the lanthanides, $R^9$, $R^{10}$, $R^{11}$, $R^{9'}$, $R^{10'}$, $R^{11'}$ are identical or different and are each hydrogen, halogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, —$OR^{13}$, —$SR^{13}$, —$N(R^{13})_2$, —$P(R^{13})_2$ or $Si(R^{13})_3$, where $R^{13}$ are identical or different and are each $C_1$-$C_{10}$-alkyl, $C_6$-$C_{15}$-aryl, $C_3$-$C_{10}$-cycloalkyl, alkylaryl, where the radicals mentioned may be partially or fully substituted by heteroatoms, $R^8$, $R^{12}$, $R^{8'}$, $R^{12'}$ are identical or different and are each $C_1$-$C_{10}$-alkyl, Y are identical or different and are each

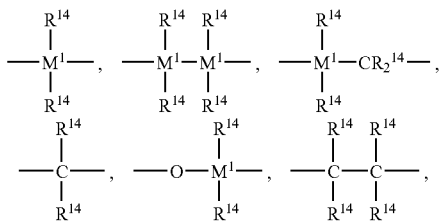

=$BR^{14}$, =$AlR^{14}$, —Ge—, —Sn—, —O—, —S—, =SO, =$SO_2$, =$NR^{14}$, =CO, =$PR^{14}$ or =$P(O)R^{14}$, where $R^{14}$ are identical or different and are each hydrogen, halogen, $C_1$-$C_{10}$-alkyl, $C_1$-$C_{10}$-fluoroalkyl, $C_6$-$C_{10}$-fluoroaryl, $C_6$-$C_{10}$-aryl, $C_1$-$C_{10}$-alkoxy, $C_2$-$C_{10}$-alkenyl, $C_7$-$C_{40}$-arylalkyl, $C_8$-$C_{40}$-arylalkenyl, $C_7$-$C_{40}$-alkylaryl or two radicals $R^{14}$ together with the atoms connecting them form a ring, and $M^1$ is silicon, germanium or tin, and X are identical or different and are each hydrogen, halogen, $C_1$-$C_{10}$-alkyl, $C_6$-$C_{15}$-aryl, alkylaryl having from 1 to 10 carbon atoms in the alkyl part and from 6 to 20 carbon atoms in the aryl part, —$OR^{17}$ or —$NR^{17}_2$, where $R^{17}$ are identical or different and are each $C_1$-$C_{10}$-alkyl, $C_6$-$C_{15}$-aryl, $C_3$-$C_{10}$-cycloalkyl, alkylaryl, and n is an integer from 1 to 4 and corresponds to the valence of M minus 2.

Preferred metals M are titanium, zirconium and hafnium, in particular zirconium.

Well-suited substituents X are fluorine, chlorine, bromine, iodine, preferably chlorine, and also C1-C6-alkyl such as methyl, ethyl, n-propyl, isopropyl, n-butyl, sec-butyl, i-butyl, preferably tert-butyl. Further well-suited substituents X are alkoxides —$OR^9$ or amides —$N(R^9)_2$ where $R^9$ are identical or different and are each $C_1$-$C_{10}$-alkyl, $C_6$-$C_{15}$-aryl, alkylaryl, arylalkyl, fluoroalkyl or fluoroaryl each having from 1 to 10 carbon atoms in the alkyl radical and from 6 to 20 carbon atoms in the aryl radical. Examples of such radicals X are methyl, ethyl, i-propyl, tert-butyl, phenyl, naphthyl, p-tolyl, benzyl, trifluoromethyl, pentafluorophenyl.

The substituents $R^9$, $R^{10}$, $R^{11}$, $R^{9'}$, $R^{10'}$, $R^{11'}$ are identical or different and are each hydrogen, fluorine, chlorine, bromine, iodine, $C_1$-$C_{20}$-alkyl, —$OR^{13}$, —$SR^{13}$, —$N(R^{13})_2$, —$P(R^{13})_2$, or $Si(R^{13})_3$, where $R^{13}$ are identical or different and are each $C_1$-$C_{10}$-alkyl, $C_6$-$C_{15}$-aryl, $C_3$-$C_{10}$-cycloalkyl, alkylaryl.

The substituents $R^9$, $R^{10}$, $R^{11}$, $R^{9'}$, $R^{10'}$, $R^{11'}$ may also be 3- to 8-membered cycloalkyl which may in turn bear a $C_1$-$C_{10}$-alkyl radical such as methyl, ethyl or propyl as substituent. Examples of such cycloalkyl radicals are cyclopropyl, cyclopentyl, preferably cyclohexyl, norbornyl, and also $C_6$-$C_{15}$-aryl such as phenyl, naphthyl; alkylaryl having from 1 to 10 carbon atoms in the alkyl part and from 6 to 20 carbon atoms in the aryl part, e.g. p-tolyl; arylalkyl having from 1 to 10 carbon atoms in the alkyl part and from 6 to 20 carbon atoms in the aryl part, e.g. benzyl, neophyl. The substituents may also be triorganosilyl $Si(R^{13})_3$ where $R^{13}$ are identical or different and are each $C_1$-$C_{20}$-alkyl, $C_3$-$C_{10}$-cycloalkyl, $C_6$-$C_{15}$-aryl, for example trimethylsilyl, tert-butyldimethylsilyl, triphenylsilyl. The radicals mentioned can of course also be partially or fully substituted by heteroatoms, for example by S-, N-, O- or halogen-containing structural elements. Examples of such substituted radicals $R^9$, $R^{10}$, $R^{11}$, $R^{9'}$, $R^{10'}$ and $R^{11'}$ are the trifluoromethyl, pentafluoroethyl, heptafluoropropyl, heptafluoroisopropyl and pentafluorophenyl groups.

Preferred substituents $R^8$, $R^{12}$, $R^{8'}$ and $R^{12'}$ are, independently of one another, $C_1$-$C_{10}$-alkyl groups such as methyl, ethyl, n-propyl, isopropyl, n-butyl, sec-butyl, i-butyl, tert-butyl, preferably simply methyl. Particular preference is given to all substituents $R^8$, $R^{12}$, $R^{8'}$ and $R^{12'}$ being identical and each being methyl.

In preferred embodiments, $R^8$, $R^{12}$, $R^{8'}$ and $R^{12'}$ and also $R^{10}$ and $R^{10'}$ in the formulae (I) and (II) are methyl, particularly preferably in combination with Y being —O—, i.e. 2,4,6-trimethylphenol is used as ligand in formula (II). Furthermore, the use of 2,6-dimethylphenol is also preferred according to the present invention.

The substituents $R^{10}$ and $R^{10'}$ can be varied within a wide range to alter the solubility of the metallocene complexes (I) resulting from the process of the present invention and, according to the present invention, are identical or different and are each hydrogen, fluorine, chlorine, bromine, iodine, preferably chlorine, alkoxides —$OR^{13}$, thiolates —$SR^{13}$, amines —$N(R^{13})_2$, —$P(R^{13})_2$ or $Si(R^{13})_3$, where $R^{13}$ are identical or different and are each $C_1$-$C_{10}$-alkyl, $C_3$-$C_{10}$-cycloalkyl, in particular 3- to 8-membered cycloalkyl which may in turn bear a $C_1$-$C_{10}$-alkyl radical such as methyl, ethyl or propyl as substituent. Examples of such cycloalkyl radicals are cyclopropyl, cyclopentyl, preferably cyclohexyl, norbornyl. Furthermore, $R^{13}$ may also be a halogen-substituted alkyl or cycloalkyl radical, for example trifluoromethyl, pentafluoroethyl, heptafluoropropyl or heptafluoroisopropyl.

A person skilled in the art will choose alkyl, cycloalkyl or aromatic groups as substituents $R^{10}$ and $R^{10'}$ in order to increase the solubility of the metallocene complexes (I) in nonpolar solvents and will choose polar substituents $R^{10}$ and $R^{10'}$, for example halogen, alkoxides, thiolates, amines and the like, to reduce the solubility of the complexes (I) in nonpolar solvents.

In the latter case, $R^{10}$ and $R^{10'}$ are preferably halogens such as chlorine or bromine, alkoxides —$OR^{13}$, thiolates —$SR^{13}$ or amines —$N(R^{13})_2$, where $R^{13}$ is methyl, ethyl, n-propyl, isopropyl, tert-butyl, cyclopropyl, cyclopentyl, cyclohexyl, norbornyl.

Very particular preference is given to $R^{13}$ being methyl. $R^{10}$ and $R^{10'}$ in the formula (II) are particularly preferably chlorine, bromine, methoxy, ethoxy, isopropyloxy, tert-butyloxy, cyclopropyloxy or cyclohexyloxy.

According to the present invention, it has been found that variation of the substituents $R^{10}$ and $R^{10'}$ over a wide range does not have an adverse effect on the racemoselectivity of the synthesis, so that the yield of the synthesis can be increased and improved in a target manner by appropriate choice of these substituents, taking into account the reaction conditions selected.

Possible briding units Y are the following:

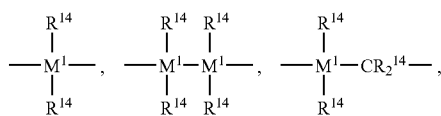

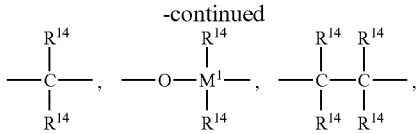

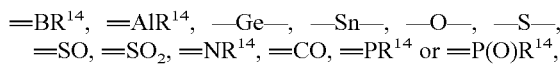

$=BR^{14}$, $=AlR^{14}$, —Ge—, —Sn—, —O—, —S—, $=SO$, $=SO_2$, $=NR^{14}$, $=CO$, $=PR^{14}$ or $=P(O)R^{14}$, where $R^{14}$ are identical or different and are each a hydrogen atom, a halogen atom, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-alkoxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or two radicals $R^{14}$ together with the atoms connecting them form a ring, and $M^1$ is silicon, germanium or tin.

Preferred bridging units Y are methylene —$CH_2$—, S, O, —$C(CH_3)_2$—; very particular preference is given to the briding units Y being identical and each being oxygen —O—.

The transition metal complexes (II) are generally prepared by methods known to those skilled in the art.

The following procedure has been found to be useful for this purpose, and is generally carried out in a temperature range from −78 to 110° C., preferably initially at about 20° C., and the reaction can then be completed by boiling under reflux. The phenol derivative is firstly deprotonated in a solvent, for example tetrahydrofuran (THF), for example by means of sodium hydride or n-butyllithium, and the transition metal compound, for example the halide such as titanium tetrachloride, zirconium tetrachloride or hafnium tetrachloride, advantageously in the form of the bis-THF adduct, is subsequently added. After the reaction is complete, the product is generally obtained by crystallization after salts have been separated off.

The bridged transition metal complexes (II) prepared according to the present invention generally still contain from 1 to 4 equivalents of a Lewis base which is generally introduced via the synthetic route. Examples of such Lewis bases are ethers such as diethyl ether or tetrahydrofuran (THF) and also amines such as TMEDA. However, it is also possible to obtain the transition metal complexes (II) free of Lewis bases, for example by drying under reduced pressure or by choosing other solvents in the synthesis. Such measures are known to those skilled in the art.

The novel racemic metallocene complexes of the formula (I) are prepared by reacting the transition metal complexes (II) with cyclopentadienyl derivatives of the alkali metals or alkaline earth metals and subsequently heating the resulting reaction mixture, in the presence or absence of free radicals or free radical formers, as described below.

Preference is given to using transition metal complexes (II) in which M is zirconium and the radicals $R^8$, $R^{8'}$, $R^{10}$, $R^{10'}$, $R^{12}$, $R^{12'}$ have the above-described, preferred meanings and Y is oxygen. Very useful complexes (II) are dichlorozirconium bis(2,6-dimethylphenoxide), dichlorozirconium bis(2,4,6-trimethylphenoxide), dichlorozirconium bis(2,6-dimethyl-4-chlorophenoxide), dichlorozirconium bis(2,6-dimethyl-4-bromophenoxide), dichlorozirconium bis(2,6-dimethyl-4-methoxyphenoxide), dichlorozirconium bis(2,6-dimethyl-4-ethoxyphenoxide), dichlorozirconium bis(2,6-dimethyl-4-tert-butoxyphenoxide) and the zirconium bisphenoxide compounds mentioned in the examples.

As cyclopentadienyl derivatives of the alkali metals or alkaline earth metals, use is made of compounds of the formula (III):

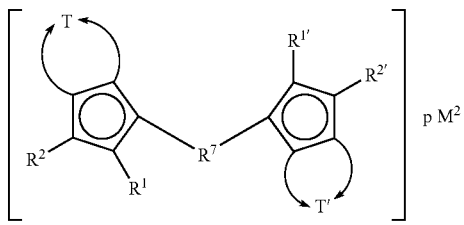

where
M² is an alkali metal ion or alkaline earth metal ion, in particular of Li, Na, K, Rb, Cs, Be, Mg, Ca, Sr or Ba, where
p=1 for Be, Mg, Ca, Sr, Ba and
p=2 for Li, Na, K, Rb, Cs, and

is a divalent group such as

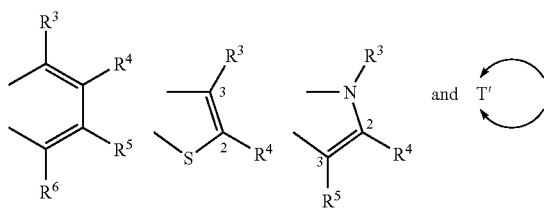

is a divalent group such as

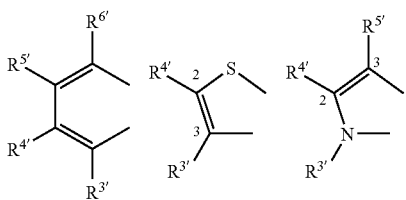

and the substituents and indices have the following meanings:
$R^1, R^2, R^3, R^4, R^5, R^6, R^{1'}, R^{2'}, R^{3'}, R^{4'}, R^{5'}, R^{6'}$ are identical or different and are each hydrogen, halogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part,
—$OR^{13}$, —$SR^{13}$, —$N(R^{13})_2$, —$P(R^{13})_2$ or $Si(R^{13})_3$, where $R^{13}$ are identical or different and are each $C_1$-$C_{10}$-alkyl, $C_6$-$C_{15}$-aryl, $C_3$-$C_{10}$-cycloalkyl, alkylaryl, where the radicals mentioned may be partially or fully substituted by heteroatoms, and $R^7$ is a -$[Z(R^{15})(R^{16})]_m$— group, where
Z can be identical or different and are each silicon, germanium, tin or carbon,
$R^{15}$, $R^{16}$ are each hydrogen, $C_1$-$C_{10}$-alkyl, $C_3$-$C_{10}$-cycloalkyl or $C_6$-$C_{15}$-aryl and
m is 1,2, 3 or 4.

Preferred compounds of the formula (III) are those in which M² is lithium, sodium and in particular magnesium. Furthermore, particular preference is given to compounds of the formula (III) in which M² is magnesium and which comprise, in particular, an indenyl-type ring system or a heteroatom-containing analog thereof.

Very particularly preferred compounds (III) are those described in the examples and also
dimethylsilanediylbis(2,4,7-trimethylindenyl)magnesium
1,2-ethanediylbis(1-{2,4,7-trimethylindenyl})magnesium
dimethylsilanediylbis(1-indenyl)magnesium
dimethylsilanediylbis(4,5,6,7-tetrahydro-1-indenyl)magnesium
dimethylsilanediylbis(2-methylindenyl)magnesium
phenyl(methyl)silanediylbis(2-methylindenyl)magnesium
diphenylsilanediylbis(2-methylindenyl)magnesium
dimethylsilanediylbis(2-methyl-4,5,6,7-tetrahydro-1-indenyl)magnesium
dimethylsilanediylbis(2,4-dimethyl-6-isopropylindenyl) magnesium
ethanediylbis(1-indenyl)magnesium
ethanediylbis(2-methyl-1-indenyl)magnesium
dimethylsilanediylbis(2-methyl-4 isopropyl-1-indenyl)magnesium
dimethylsilanediylbis(2-methyl-4-phenyl-1-indenyl)magnesium
dimethylsilanediylbis(2-methyl-4-naphthyl-1-indenyl)magnesium
dimethylsilanediylbis(2-methyl-4-{3,5-trifluoromethyl}phenyl-1-indenyl)magnesium
dimethylsilanediylbis(2-ethyl-4-isopropyl-1-indenyl)magnesium
dimethylsilanediylbis(2-ethyl-4-phenyl-1-indenyl)magnesium
dimethylsilanediylbis(2-ethyl-4-naphthyl-1-indenyl)magnesium
dimethylsilanediylbis(2-ethyl-4-{3,5-trifluoromethyl}phenyl-1-indenyl)magnesium
ethanediylbis(2-methyl-4-phenyl-1-indenyl)magnesium
ethanediylbis(2-methyl-4-naphthyl-1-indenyl)magnesium
ethanediylbis(2-methyl-4-{3,5-di(trifluoromethyl)}phenyl-1-indenyl)magnesium
dimethylsilanediylbis(2-methyl-4-(4'-tert-butylphenyl)indenyl)magnesium
dimethylsilanediylbis(2-methyl-4-(4'-tert-butylphenyl)indenyl)-(2-isopropyl-4-(4'-tert-butylphenyl)indenyl)magnesium
dimethylsilanediylbis(2-cyclohexyl-4-phenylindenyl)magnesium
dimethylsilanediylbis(2-butyl-4-phenylindenyl)magnesium
dimethylsilanediylbis(2-ethyl-4-(4'-tert-butylphenyl)indenyl)magnesium
dimethylsilanediylbis(2-propyl-4-(4'-tert-butylphenyl)indenyl)magnesium
dimethylgermanediylbis(2-meth-4-(4'-tert-butylphenyl)indenyl)magnesium diethylsilanediylbis(2-methyl-4-(4'-tert-butylphenyl)indenyl)magnesium
dimethylsilanediylbis(2-butyl-4-(4'-tert-butylphenyl)indenyl)magnesium
dimethylsilanediyl(2-methyl-4-(4'-tert-butylphenyl)indenyl)-(4-(4'-tert-butylphenyl)indenyl)magnesium
dimethylsilanediylbis(2-butyl-4-(4'-tert-butylphenyl-6-(4'-tert-butylphenyl)indenyl)magnesium
dimethylsilanediylbis(2-isopropyl-4-(4'-tert-butylphenyl)indenyl)magnesium
dimethylsilanediylbis(2-isopropyl-4-(4'-tert-butylphenyl)indenyl)magnesium
dimethylsilanediyl(2-ethyl-4-(4'-tert-butylphenyl)indenyl)-2-isopropyl-4-(4'-tert-butylphenyl)indenyl)magnesium
dimethylsilanediyl(2-methyl-4-naphthylindenyl)-(2-isopropyl-4-(4-tert-butylphenyl)indenyl)magnesium and also
dimethylsilanediylbis(2,4,7-trimethylindenyl)dilithium
1,2-ethanediylbis(1-{2,4,7-trimethylindenyl})dilithium
dimethylsilanediylbis(1-indenyl)dilithium
dimethylsilanediylbis(4,5,6,7-tetrahydro-1-indenyl)dilithium
dimethylsilanediylbis(2-methylindenyl)dilithium
phenyl(methyl)silanediylbis(2-methylindenyl)dilithium
diphenylsilanediylbis(2-methylindenyl)dilithium
dimethylsilanediylbis(2-methyl-4,5,6,7-tetrahydro-1-indenyl)dilithium
dimethylsilanediylbis(2,4-dimethyl-6-isopropylindenyl)dilithium ethanediylbis(1-indenyl)dilithium
ethanediylbis(2-methyl-1-indenyl)dilithium
dimethylsilanediylbis(2-methyl-4 isopropyl-1-indenyl)dilithium
dimethylsilanediylbis(2-methyl-4-phenyl-1-indenyl)dilithium
dimethylsilanediylbis(2-methyl-4-naphthyl-1-indenyl)dilithium
dimethylsilanediylbis(2-methyl-4-{3,5-trifluoromethyl}phenyl-1-indenyl)dilithium
dimethylsilanediylbis(2-ethyl-4-isopropyl-1-indenyl)dilithium
dimethylsilanediylbis(2-ethyl-4-phenyl-1-indenyl)dilithium
dimethylsilanediylbis(2-ethyl-4-naphthyl-1-indenyl)dilithium
dimethylsilanediylbis(2-ethyl-4-{3,5-trifluoromethyl}phenyl-1-indenyl)dilithium
ethanediylbis(2-methyl-4-phenyl-1-indenyl)dilithium
ethanediylbis(2-methyl-4-naphthyl-1-indenyl)dilithium
ethanediylbis(2-methyl-4-{3,5-di-(trifluoromethyl)}phenyl-1-indenyl)dilithium
dimethylsilanediylbis(2-methyl-4-(4'-tert-butyl-phenyl)indenyl)dilithium
dimethylsilanediylbis(2-methyl-4-(4'-tert-butylphenyl)indenyl)-(2-isopropyl-4-(4'-tert-butylphenyl)indenyl)dilithium
dimethylsilanediylbis(2-cyclohexyl-4-phenylindenyl)dilithium
dimethylsilanediylbis(2-butyl-4-phenylindenyl)dilithium
dimethylsilanediylbis(2-ethyl-4-(4'-tert-butylphenyl)indenyl)dilithium
dimethylsilanediylbis(2-propyl-4'-tert-butylphenyl)indenyl)dilithium
dimethylgermanediylbis(2-meth-4-(4'-tert-butylphenyl)indenyl)dilithium
diethylsilanediylbis(2-methyl-4-(4'-tert-butylpheny)indenyl)dilithium
dimethylsilanediylbis(2-butyl-4-(4'-tert-butylphenyl)indenyl)dilithium
dimethylsilanediyl(2-methyl-4-(4'-tert-butylphenyl)indenyl)-(4-(4'-tert-butyl-phenyl)indenyl)dilithium
dimethylsilanediylbis(2-butyl-4-(4-tert-butylphenyl-6-(4'-tert-butylphenyl)indenyl)dilithium
dimethylsilanediylbis(2-isopropyl-4-(4'-tert-butylphenyl)indenyl)dilithium
dimethylsilanediylbis(2-isopropyl-4-(4'-tert-butylphenyl)indenyl)dilithium
dimethylsilanediyl(2-ethyl-4-(4-tert-butylphenyl)indenyl)-2-isopropyl-4-(4'-tert-butylphenyl)indenyl)dilithium
dimethylsilanediyl(2-methyl-4-naphthylindenyl)-(2-isopropyl-4-(4'-tert-butyl-phenyl)indenyl)dilithium and also the respective Lewis base adducts of these compounds with, for example, THF, DME, TMEDA Such alkali metal or alkaline earth metal compounds (III) can be obtained by methods known from the literature, for example by the preferably stoichiomebtic, reaction of an organometallic compound or a hydride of an alkali metal or alkaline earth metal with the corresponding cyclopentadienyl-type hydrocarbon. Suitable organometallic compounds are, for example, n-butyllithium, di-n-butylmagnesium and (n,s)-dibutylmagnesium.

The reaction of the transition metal complexes (II) with the cyclopentadienyl derivatives of alkali metals or alkaline earth metals of the formula (III) usually takes place in an organic solvent or suspension medium, preferably in a solvent mixture comprising a Lewis-basic solvent, in a temperature range from −78° C. to 250° C., preferably from 0 to 110° C. Well-suited solvents are aliphatic hydrocarbons such as pentane, hexane, heptane, aromatic hydrocarbons such as toluene, ortho-, meta- or para-xylene or isopropylbenzene (cumene), ethers such as tetrahydrofuran (THF), diethyl ether, methyl tert-butyl ether or dimethoxyethane (DME), amines such as diisopropylamine, tetramethylethanediamine (TMEDA) or pyridine.

Well-suited solvent mixtures are mixtures of toluene and THF, toluene and DME or toluene and TMEDA, with the Lewis base generally being present in an amount of from 0.1 to 50 mol %, preferably from 1 to 20 mol %, based on the solvent mixture. The molar ratio of the transition metal complex (I) to the cyclopentadienyl derivative of an alkali metal or alkaline earth metal (III) is usually in the range from 0.8:1 to 1:1.2, preferably 1:1.

In a particularly preferred embodiment, the process of the present invention for preparing racemic metallocene complexes of the formula (I)

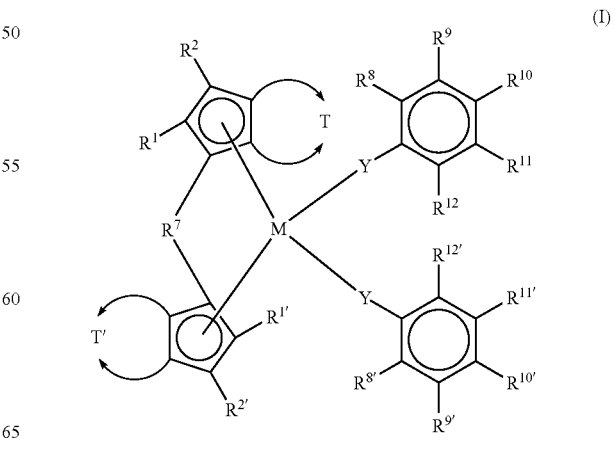

comprises the following steps:
a) deprotonation of a compound of the formula (IV)

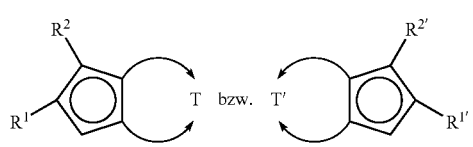

(IV)

by means of a suitable deprotonating agent;
b) reaction of the deprotonated compound (IV) with a compound $R^7Hal_2$, where Hal is a halogen substituent such as F, Cl, Br or I, and subsequent repeat deprotonation by means of a suitable deprotonating agent to give the compound of the formula (III)

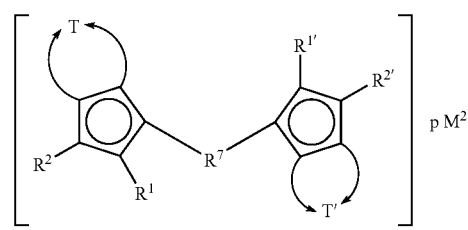

(III)

where
$M^2$ is an alkali metal ion or alkaline earth metal ion,
where
p is 1 when $M^2$ is an alkaline earth metal ion and is 2 when $M^2$ is an alkali metal ion, and $R^7$ is as defined above;
c) reaction of the compound of the formula (III) with a transition metal complex of the formula (II)

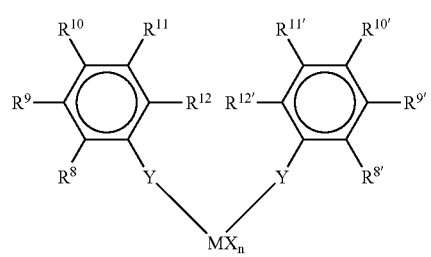

(II)

where
X are identical or different and are each hydrogen, halogen, $C_1$-$C_{10}$-alkyl, $C_6$-$C_{15}$-aryl, alkylaryl having from 1 to 10 carbon atoms in the alkyl part and from 6 to 20 carbon atoms in the aryl part, —$OR^{17}$ or
—$NR^{17}_2$, where $R^{17}$ are identical or different and are each $C_1$-$C_{10}$-alkyl, $C_6$-$C_{15}$-aryl, $C_3$-$C_{10}$-cycloalkyl, alkylaryl,
n is an integer from 1 to 4 and corresponds to the valence of M minus 2, and the other substituents are as defined above,
with all substituents and their preferred ranges being as defined above.

Examples of suitable deprotonating agents are, as mentioned above, n-butyllithium, tert-butyllithium, sodium hydride, potassium tert-butoxide, Grignard reagents of magnesium, magnesium compounds such as di-n-butylmagnesium, (n,s)-dibutylmagnesium or other suitable alkaline earth metal alkyl or alkali metal alkyl compounds.

The racemic metallocene complexes of the present invention are preferably compounds of the formula (I)

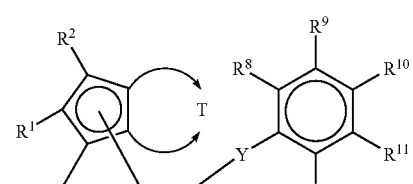

(I)

where

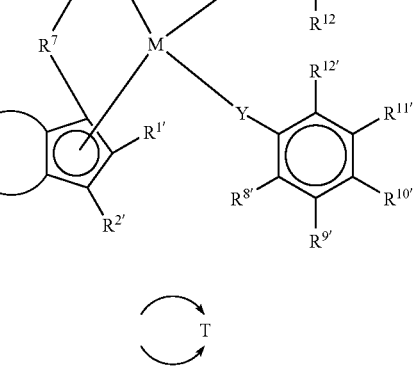

is a divalent group such as

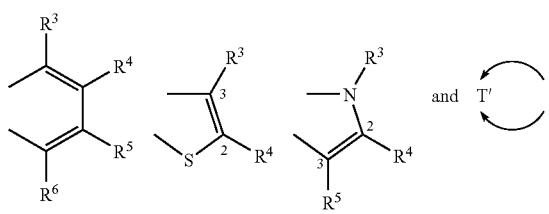

is a divalent group such as

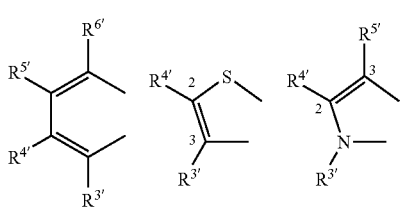

where the substituents are as defined above.

Preferred compounds of the formula (I) are those in which M is titanium, hafnium and in particular zirconium. Particularly preferred compounds of the formula (I) are metallocenes in which an indenyl-type ring system which is unsubstituted or methyl-substituted in the 2 position is present Very particular preference is given to compounds of the formula (I) in which are

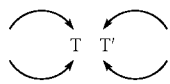

and

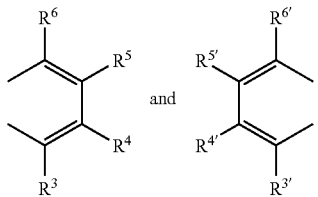

and the radicals R³ to R⁶ and R³' to R⁶' are as defined above.

Most preferred compounds (I) are those which are described in the examples, in particular
dimethylsilylbis(1-indenyl)zirconium bis(2,4,6-trimethylphenoxide),
dimethylsilylbis(2-methyl-1-indenyl)zirconium bis(2,4,6-trimethylphenoxide),
dimethylsilylbis(2-methyl-1-indenyl)zirconium bis(2,6-dimethylphenoxide),
dimethylsilylbis(2-methyl-1-indenyl)zirconium bis(2,6-dimethyl-4-bromophenoxide), or ethanediylbis(1-indenyl)zirconium bis(2,4,6-trimethylphenoxide), and also:
dimethylsilanediylbis(2,4,7-trimethylindenyl)zirconium bis (2,6-dimethylphenoxide);
1,2-ethanediylbis(1-{2,4,7-trimethylindenyl})zirconium bis (2,6-dimethylphenoxide);
dimethylsilanediylbis(1-indenyl)zirconium bis(2,6-dimethylphenoxide);
dimethylsilanediylbis(4,5,6,7-tetrahydro-1-indenyl)zirconium bis(2,6-dimethylphenoxide);
dimethylsilanediylbis(2-methylindenyl)zirconium bis(2,6-dimethylphenoxide);
phenyl(methyl)silanediylbis(2-methylindenyl)zirconium bis (2,6-dimethylphenoxide);
diphenylsilanediylbis(2-methylindenyl)zirconium bis(2,6-dimethylphenoxide);
dimethylsilanediylbis(2-methyl-4,5,6,7-tetrahydro-1-indenyl)zirconium bis(2,6-dimethylphenoxide);
dimethylsilanediylbis(2,4-dimethyl-6-isopropylindenyl)zirconium bis(2,6-dimethylphenoxide);
dimethylsilanediylbis(2-methyl-4-isopropyl-1-indenyl)zirconium bis(2,6-dimethylphenoxide);
dimethylsilanediylbis(2-methyl-4-phenyl-1-indenyl)zirconium bis(2,6-dimethylphenoxide);
dimethylsilanediylbis(2-methyl-4-naphthyl-1-indenyl)zirconium bis(2,6-dimethylphenoxide);
dimethylsilanediylbis(2-methyl-4-{3,5-trifluoromethyl}phenyl-1-indenyl)zirconium bis(2,6-dimethylphenoxide);
dimethylsilanediylbis(2-ethyl-4-isopropyl-1-indenyl)zirconium bis(2,6-dimethylphenoxide);
dimethylsilanediylbis(2-ethyl-4-phenyl-1-indenyl)zirconium bis(2,6-dimethylphenoxide);
dimethylsilanediylbis(2-ethyl-4-naphthyl-1-indenyl)zirconium bis(2,6-dimethylphenoxide);
dimethylsilanediylbis(2-ethyl-4-{3,5-trifluoromethyl}phenyl-1-indenyl)zirconium bis(2,6-dimethylphenoxide);
ethanediylbis(2-methyl-4-phenyl-1-indenyl)zirconium bis (2,6-dimethylphenoxide);
ethanediylbis(2-methyl-4-naphthyl-1-indenyl)zirconium bis (2,6-dimethylphenoxide);
ethanediylbis(2-methyl-4-{3,5-di(trifluoromethyl)}phenyl-1-indenyl)zirconium bis(2,6-dimethylphenoxide);
dimethylsilanediylbis(2-methyl-4-(4'-tert-butylphenyl)indenyl)zirconium bis(2,6-dimethylphenoxide);
dimethylsilanediyl(2-methyl-4-(4'-tert-butylphenyl)indenyl)(2-isopropy-4-(4'-tert-butylphenyl)indenyl)zirconium bis(2,6-dimethylphenoxide);
dimethylsilanediylbis(2-cyclohexyl-4-phenylindenyl)zirconium bis(2,6-dimethylphenoxide);
dimethylsilanediylbis(2-butyl-4-phenylindenyl)zirconium bis(2,6-dimethylphenoxide);
dimethylsilanediylbis(2-ethyl-4-(4'-tert-butylphenyl)indenyl)zirconium bis(2,6-dimethylphenoxide);
dimethylsilanediylbis(2-propyl-4-(4'-tert-butylphenyl)indenyl)zirconium bis(2,6-dimethylphenoxide);
dimethylgermanediylbis(2-methyl-4-(4'-tert-butylphenyl) indenyl)zirconium bis(2,6-dimethylphenoxide);
diethylsilanediylbis(2-methyl-4-(4'-tert-butylpheny)indenyl)zirconium bis(2,6-dimethylphenoxide);
dimethylsilanediylbis(2-butyl-4-(4'-tert-butylphenyl)indenyl)zirconium bis(2,6-dimethylphenoxide);
dimethylsilanediyl(2-methyl-4-(4'-tert-butylphenyl)indenyl)-4-(4'-tert-butylphenyl)indenyl)zirconium bis(2,6-dimethylphenoxide);
dimethylsilanediylbis(2-butyl-4-(4'-tert-butylphenyl)-6-(4'-tert-butyl-phenyl)indenyl)zirconium bis-(2,6-dimethylphenoxide);
dimethylsilanediylbis(2-isopropyl-4-(4'-tert-butylphenyl)indenyl)zirconium bis(2,6-dimethylphenoxide);
dimethylsilanediyl(2-ethyl-4-(4'-tert-butylphenyl)indenyl) (2-isopropyl-4-(4'-tert-butyl-phenyl)indenyl)zirconium bis(2,6-dimethylphenoxide); or
dimethylsilanediyl(2-methyl-4-naphthylindenyl)(2-isopropyl-4-(4'-tert-butyl-phenyl)indenyl)zirconium bis(2,6-dimethylphenoxide);
dimethylsilanediylbis(2,4,7-trimethylindenyl)zirconium bis (2,4,6-trimethylphenoxide);
1,2-ethanediylbis(1-{2,4,7-trimethylindenyl})zirconium bis (2,4,6-trimethylphenoxide); dimethylsilanediylbis(1-indenyl)zirconium bis(2,4,6-trimethylphenoxide);
dimethylsilanediylbis(4,5,6,7-tetrahydro-1-indenyl)zirconium bis(2,4,6-trimethylphenoxide);
dimethylsilanediylbis(2-methylindenyl)zirconium bis(2,4,6-trimethylphenoxide);
phenyl(methyl)silanediylbis(2-methylindenyl)zirconium bis (2,4,6-trimethylphenoxide);
diphenylsilanediylbis(2-methylindenyl)zirconium bis(2,4,6-trimethylphenoxide);
dimethylsilanediylbis(2-methyl-4,5,6,7-tetrahydro-1-indenyl)zirconium bis(2,4,6-trimethylphenoxide);
dimethylsilanediylbis(2,4-dimethyl-6-isopropylindenyl)zirconium bis(2,4,6-trimethylphenoxide);
dimethylsilanediylbis(2-methyl-4-isopropyl-1-indenyl)zirconium bis(2,4,6-trimethylphenoxide);
dimethylsilanediylbis(2-methyl-4-phenyl-1-indenyl)zirconium bis(2,4,6-trimethylphenoxide);
dimethylsilanediylbis(2-methyl-4-naphthyl-1-indenyl)zirconium bis(2,4,6-trimethylphenoxide);
dimethylsilanediylbis(2-methyl-4-{3,5-trifluoromethyl}phenyl-1-indenyl)zirconium bis(2,4,6-trimethylphenoxide);
dimethylsilanediylbis(2-ethyl-4-isopropy-1-indenyl)zirconium bis(2,4,6-trimethylphenoxide);

dimethylsilanediylbis(2-ethyl-4-phenyl-1-indenyl)zirconium bis(2,4,6-trimethylphenoxide);
dimethylsilanediylbis(2-ethyl-4-naphthyl-1-indenyl)zirconium bis(2,4,6-trimethylphenoxide);
dimethylsilanediylbis(2-ethyl-4-{3,5-trifluoromethyl}phenyl-1-indenyl)zirconium bis(2,4,6-trimethylphenoxide);
ethanediylbis(2-methyl-4-phenyl-1-indenyl)zirconium bis(2,4,6-trimethylphenoxide);
ethanediylbis(2-methyl-4-naphthyl-1-indenyl)zirconium bis(2,4,6-trimethylphenoxide);
ethanediylbis(2-methyl-4-{3,5-di(trifluoromethyl)}phenyl-1-indenyl)zirconium bis(2,4,6-trimethylphenoxide);
dimethylsilanediylbis(2-methyl-4-(4'-tert-butylphenyl)indenyl)zirconium bis(2,4,6-trimethylphenoxide);
dimethylsilanediyl(2-methyl-4-(4'-tert-butylphenyl)indenyl)(2-isopropyl-4-(4'-tert-butyl-phenyl)indenyl)zirconium bis(2,4,6-trimethylphenoxide);
dimethylsilanediylbis(2-cyclohexyl-4-phenylindenyl)zirconium bis(2,4,6-trimethylphenoxide);
dimethylsilanediylbis(2-butyl-4-phenylindenyl)zirconium bis(2,4,6-trimethylphenoxide);
dimethylsilanediylbis(2-ethyl-4-(4'-tert-butylphenyl)indenyl)zirconium bis(2,4,6-trimethylphenoxide);
dimethylsilanediylbis(2-propyl-4-(4'-tert-butylphenyl)indenyl)zirconium bis(2,4,6-trimethylphenoxide);
dimethylgermanediylbis(2-methyl-4-(4'-tert-butylphenyl)indenyl)zirconium bis(2,4,6-trimethylphenoxide);
diethylsilanediylbis(2-methyl-4-(4'-tert-butylphenyl)indenyl)zirconium bis(2,4,6-trimethylphenoxide);
dimethylsilanediylbis(2-butyl-4-(4'-tert-butylphenyl)indenyl)zirconium bis(2,4,6-trimethylphenoxide);
dimethylsilanediyl(2-methyl-4-(4'-tert-butylphenyl)indenyl-4-(4'-tert-butyl-phenyl)indenyl)zirconium bis(2,4,6-trimethylphenoxide);
dimethylsilanediylbis(2-butyl-4-(4'-tert-butylphenyl)-6-(4'-tert-butylphenyl)indenyl)zirconium bis(2,4,6-trimethylphenoxide);
dimethylsilanediylbis(2-isopropyl-4-(4'-tert-butylphenyl)indenyl)zirconium bis(2,4,6-trimethylphenoxide);
dimethylsilanediyl(2-ethyl-4-(4'-tert-butylphenyl)indenyl)(2-isopropyl-4-(4'-tert-butyl-phenyl)indenyl)zirconium bis(2,4,6-trimethylphenoxide); or
dimethylsilanediyl(2-methyl-4-naphthylindenyl)(2-isopropyl(4'-tert-butylphenyl)indenyl)zirconium bis(2,4,6-trimethylphenoxide).

The racemic metallocene complexes, preferably those of the formula (I), can generally be modified further.

In particular, the phenoxide ligands in the complex (I) can, for example, be replaced either individually or together in a substitution reaction and the split-off ligands can, if appropriate, be reused. Suitable substitution methods are reaction of the racemic metallocene complexes, preferably those of the formula (I), with $SOCl_2$, silicon tetrachloride, methylaluminum dichloride, dimethylaluminum chloride, aluminum trichloride, dialkylaluminum chlorides, aluminum sesquichlorides, particularly preferably ethylaluminum dichloride, or a Brönsted acid such as a hydrogen halide, i.e. HF, HBr, HI, preferably HCl, which is generally employed as such or as a solution in water or organic solvents such as diethyl ether, THF. Well-suited solvents are aliphatic hydrocarbons such as pentane, hexane, heptane, aromatic hydrocarbons such as toluene, ortho-, meta- or para-xylene or isopropylbenzene (cumene), ethers such as tetrahydrofuran (THF), diethyl ether, methyl tert-butyl ether or dimethoxyethane (DME), amines such as diisopropylamine, tetramethylethane-diamine (TMEDA) or pyridine.

Lewis base-containing solvent mixtures of hydrocarbons and ethers or amines or both, for example mixtures of toluene and THF, toluene and DME or toluene and TMEDA, are very useful, with the Lewis base generally being present in an amount of 0.01-50 mol %, preferably 0.1-10 mol %, based on the solvent mixture. Particularly well-suited "replacement reagents" are carboxylic acid halides such as acetyl chloride, phenylacetyl chloride, 2-thiophenacetyl chloride, trichloroacetyl chloride, trimethylacetyl chloride, O-acetylmandelyl chloride, 1,3,5-benzenetricarboxylic chloride, 2,6-pyridinecarboxylic chloride, tert-butylacetyl chloride, chloroacetyl chloride, 4-chlorophenylacetyl chloride, dichloroacetyl chloride; 3-methoxyphenylacetyl chloride, acetyl bromide, bromoacetyl bromide, acetyl fluoride, benzoyl fluoride. These are generally used in the abovementioned solvents or else as such.

This usually gives the monohalide or dihalide analogous to the compound of the formula (I), i.e. the compound of the formula (Ia):

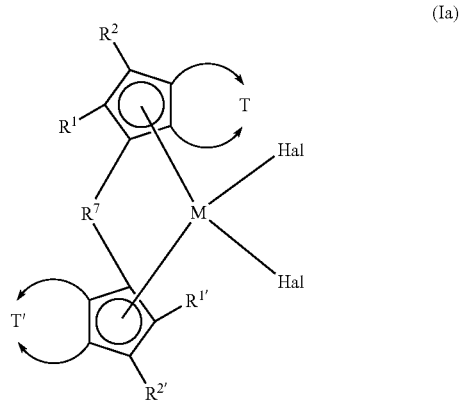

(Ia)

where Hal is F, Cl, Br or I.

A further well-suited substitution method is reaction of the racemic metallocene complexes of the formula (I) with organoaluminum compounds such as tri-$C_1$-$C_{10}$-alkylaluminums, i.e. trimethylaluminum, triethylaluminum, tri-n-butylaluminum, triisobutylaluminum. According to the present state of knowledge, this generally gives the organo compound analogous to the compound II (organic radicals in place of the bisphenoxide, e.g. $C_1$-$C_{10}$-alkyl such as methyl, ethyl, n-butyl, i-butyl) and, for example, the organoaluminum bisnaphthoxide.

In the replacement reactions, the components are usually used in a stoichiometric ratio, depending on whether a monosubstituted or disubstituted product is to be obtained.

The replacement reactions generally take place with retention of the stereochemistry of the metallocene complexes, i.e. it is generally the case that no transformation of the racemic form into the meso form of the metallocene complexes takes place.

The process of the present invention makes it possible for the rac form of metallocene complexes (I) and also the corresponding dihalides (Ia) obtainable therefrom to be obtained very selectively. Novel bisphenoxide complexes of the bisindenyl-metallocene type which have hydrogen or a ligand different from hydrogen in the vicinity of the bridging unit $R^7$ (namely the 2-position) can be obtained particularly advantageously.

The racemic metallocene complexes (I) can be obtained selectively by the process of the present invention regardless of the presence or absence of a substituent in the 2 position on the indenyl system. Furthermore, the process of the present invention makes it possible for the solubility of the resulting products to be controlled in a simple fashion by selection of the substituent in the 4 position on the phenoxide ligand ($R^{10}$ or $R^{10'}$), which makes isolation of the products easier and increases the yields of the synthesis.

A further significant advantage is that the process of the present invention can be carried out racemoselectively as a single-vessel process. For the purposes of the present invention, a single-vessel process means that no intermediates are isolated after the individual process steps. The further reaction can be carried out directly using the reaction product mixtures from the preceding step.

The racemic metallocene complexes of the present invention, in particular those of the formula (I) or their above-described derivatives of the formula (Ia) which are obtainable, for example, by replacement of the phenoxide ligands, can be used as catalysts or in catalyst systems for the Polymerization of olefinically unsaturated compounds such as ethylene, propylene, 1-butene, 1-hexene, 1-octene, styrene. They are particularly advantageous for the stereoselective polymerization of prochiral, olefinically unsaturated compounds such as propylene and styrene. Suitable catalysts or catalyst systems in which the racemic metallocene complexes of the present invention can function as "metallocene component" are usually obtained by means of compounds capable of forming metallocenium ions, as described, for example, in EP-A-0 700 935, page 7, line 34, to page 8, line 21, and the formulae (IV) and (V) therein. Further compounds capable of forming metallocenium ions are aluminoxanes $(RAlO)_n$ such as methylaluminoxane, and also boron activators.

The racemic metallocene complexes of the present invention, in particular those of the formula (I) or their above-described derivatives of the formula (Ia) obtainable by, for example, replacement of the phenoxide ligands, can also be used as reagents or as catalysts or in catalyst systems in stereoselective, in particular organic, synthesis. Examples which may be mentioned are stereoselective reductions or stereoselective alkylations of C=C double bonds or C=O or C=N double bonds.

EXAMPLES

General procedures, preparation and handling of the organometallic compounds were carried out in the absence of air and moisture under argon (Schlenk technique or glove box). All solvents required were purged with argon and dried over molecular sieves before use.

The preparation of the bridged bisindenyl ligands was carried out by the customary methods known to those skilled in the art from the prior art; some of the bisindenyls used are also commercially available compounds. The BuLi solution used had a concentration of about 20% by weight of butyllithium in toluene (about 2.6 molar).

Example 1

Preparation of ethanediylbis(indenyl)zirconium bis(2,4,6-trimethylphenoxide)

a) Preparation of $ZrCl_4(THF)_2$

In a dry 1000 ml three-necked round-bottom flask which had been flushed with inert gas and was provided with a magnetic stirrer bar, dropping funnel and vacuum connection with stopcock, 46.6 g (199.97 mmol) of $ZrCl_4$ were suspended in 80 g of toluene. The suspension was cooled to about 4° C. in an ice bath, and 30.3 g of THF were then slowly added dropwise via the dropping funnel. The resulting suspension was allowed to warm to room temperature and was stirred for one hour.

b) Preparation of $Li(2,4,6-Me_3-C_6H_2O)$

In a dry 1000 ml three-neck round-bottom flask which had been flushed with inert gas and was provided with a magnetic stirrer bar, dropping funnel and vacuum connection with stopcock, 56.3 g (413.42 mmol) of 2,4,6-trimethylphenol were dissolved in 100 g of toluene and 29 g of THF. The solution was cooled to about 4° C. in an ice bath and 124.3 ml of BuLi solution were subsequently added via the dropping funnel over a period of 1 hour. The reaction mixture was then allowed to warm to room temperature and was stirred for one hour.

c) Preparation of $(THF)_2Cl_2Zr(2,4,6-Me_3-C_6H_2O)$

The solution from step a) was transferred under nitrogen by means of a syringe into the suspension from step b) at room temperature over a period of several minutes. The reaction mixture was stirred at room temperature for 2.5 hours.

d) Preparation of $Li_2[1,2\text{-ethanediylbis(indenyl)}]$

In a dry 1000 ml three-neck round-bottom flask which had been flushed with inert gas and was provided with a magnetic stirrer bar, dropping funnel and vacuum connection with stopcock, 46.5 g (179.98 mmol) of 1,2-ethanediylbis(indenyl) were suspended in 80 g of toluene and 17.1 g of THF. The suspension was cooled in an ice bath and 112.5 g of a BuLi solution were slowly added dropwise over a period of 20 minutes while stirring. The resulting suspension was stirred at room temperature for a further 2.5 hours.

e) Preparation of 1,2-ethanediylbis(indenyl)$Zr(2,4,6-Me_3-C_6H_2O)_2$

The suspension from step c) was transferred under nitrogen by means of a syringe into the suspension from step d) over a period of several minutes. The resulting suspension was stirred at room temperature for 1 hour. A $^1$H-NMR spectrum of the reaction mixture showed the racemoselective formation of the target complex. The reaction mixture was stirred overnight at room temperature, subsequently heated to 60° C. and, at this temperature, transferred by means of a syringe to a glass filter frit number 4 and filtered into a round-bottom flask with stopcock. The precipitate was washed twice with 40 g and 35 g of toluene and the filtrate was subsequently concentrated under reduced pressure. 123 g of solvent were removed. The complex crystallized at room temperature after a number of hours. The precipitate was filtered off, washed with 5 ml of toluene and dried under reduced pressure. This gave a total of 15.61 g of the target compound in pure rac form, as was established by means of $^1$H-NMR. Yield: 52%.

Elemental analysis:

|  | calculated: | found: |
|---|---|---|
| C % | 73.86 | 73.2 |
| H % | 6.2 | 6.2 |

Example 2

Preparation of dimethylsilylbis(indenyl)zirconium bis(2,4,6-trimethylphenoxide)

a) Preparation of $ZrCl_4(THF)_2$

The preparation was carried out as described in step a) of example 1, but the amounts used were 9.33 g of $ZrCl_4$ (40.03 mmol), 140 ml of toluene and 7 g of THF.

b) Preparation of $Li(2,4,6-Me_3-C_6H_2O)$

The preparation was carried out as described in step b) of example 1, but the amounts used were: 10.90 g (80.04 mmol) of 2,4,6-trimethylphenol, 140 ml of toluene, 5.77 g of THF and 29.0 ml of BuLi solution.

c) Preparation of $(THF)_2Cl_2Zr(2,4,6-Me_3-C_6H_2O)_2$

The suspension from step a) was transferred under nitrogen by means of a syringe into the suspension from step c) at room temperature over a period of several minutes. The reaction mixture was stirred at room temperature for three hours.

d) Preparation of $Me_2Si(ind)_2Li_2$

This reaction step was carried out as described in example 1, d). The amounts used were 11.0 g (38.13 mmol) of dimethylsilylbis(indenyl) in 120 ml of toluene and 7 g of THF. 29 ml of BuLi solution were added, and the mixture was subsequently stirred at room temperature for another 1.5 hours.

e) Preparation of $Me_2Si(ind)_2Zr(2,4,6-Me_3-C_6H_2O)_2$

The suspension from step c) was transferred under nitrogen by means of a syringe into the suspension from step d) over a period of several minutes. The resulting suspension was stirred at room temperature for three hours. $^1$H-NMR spectroscopy indicated racemoselective formation of the complex. The reaction mixture was stirred overnight at room temperature, then heated at 80° C. for 1 hour and subsequently filtered under nitrogen through a glass filter frit number 4 which was blanketed with inert gas into a round-bottom flask with stopcock and the filtrate was concentrated to about 50 ml under reduced pressure. The target complex crystallized out at room temperature after 12 hours and was isolated by filtration, washed with small amounts of toluene and dried under reduced pressure. This gave a total of 16.0 g of the target complex in the pure rac form; yield: 64%.

Elemental analysis:

|     | calculated: | found: |
| --- | --- | --- |
| C % | 70.43 | 70.5 |
| H % | 6.22 | 6.5 |

Example 3

Preparation of dimethylsilylbis(2-methylindenyl)zirconium bis(2,6-dimethylphenoxide)

a) Preparation of $ZrCl_4(THF)$

The preparation was carried out as described in example 1 a) using the following amounts: 5.05 g (21.67 mmol) of $ZrCl_4$, 90 ml of toluene and 4.0 g of THF.

b) Preparation of $Li(2,6-Me_2-C_6H_2O)$

The preparation was carried out as described in example 1 b) using the following amounts and materials: 5.29 g of 2,6-dimethylphenol, 100 ml of toluene, 4.0 g of THF and 16.5 ml of BuLi solution.

c) Preparation of $(THF)_2Cl_2Zr(2,6-Me_2-C_6H_2O)_2$

The suspension from b) was transferred under nitrogen by means of a syringe into the white suspension from step a) at room temperature over a period of several minutes. The reaction mixture was stirred at room temperature for 6 hours.

d) Preparation of $Me_2Si(2-Me-ind)_2Li_2$

In a dry 1000 ml three-neck round-bottom flask which had been flushed with inert gas and was provided with a magnetic stirrer bar, dropping funnel and vacuum connection with stopcock, 6.6 g (20.85 mmol) of dimethylsilylbis(2-methylindenyl) were suspended in 100 ml of toluene and 6.0 g of THF. 16 ml of BuLi solution were slowly added dropwise at room temperature. The suspension was stirred at room temperature for another 2.5 hours.

e) Preparation of $Me_2Si(2-Me-ind)_2Zr(2,6-Me_2-C_6H_2O)_2$

The suspension from step c) was transferred under nitrogen by means of a syringe into the suspension from step d) over a period of several minutes. The resulting suspension was stirred at room temperature for 12 hours. A $^1$H-NMR spectrum showed that the target complex had formed in a rac/meso ratio of about 13.5:1. The suspension was stirred at room temperature for a further 4 days, subsequently heated to 80° C. and filtered under nitrogen through a glass filter frit No. 4. The residue was washed with 120 ml of toluene at 80° C., and the filtrate was subsequently evaporated to about 50 ml at 40° C. under reduced pressure. After 12 hours at room temperature, the complex crystallized out. The crystals were filtered off, washed with small amounts of toluene and dried under reduced pressure. This gave a total of 11.33 g of the target compound; yield: 83%.

Example 4

Preparation of dimethylsilylbis(2-methylindenyl)zirconium bis(2,4,6-trimethylphenoxide)

a) Preparation of $ZrCl_4(DME)$

The synthesis of the zirconium tetrachloride-DME adduct was carried out by a method similar to a) of example 1 using DME in place of THF. The amounts used were: 10.6 g (45.48 mmol) of zirconium tetrachloride, 50.0 g of toluene, 5.7 g of DME.

b) Preparation of $Li(2,4,6-Me_3-C_6H_2O)_2$

The preparation was carried out as in example 1 b); the amounts used were: 12.4 g (91.05 mmol) of 2,4,6-trimethylphenol, 47 g of toluene, 8 g of DME in place of THF, and 28.3 g of a 20% strength by weight BuLi solution.

c) Preparation of $(DME)Cl_2Zr(2,4,6-Me_3-C_6H_2O)_2$

The suspension from step b) was transferred under nitrogen by means of a syringe into the suspension from step a) at room temperature over a period of several minutes. The reaction mixture was stirred at room temperature for 1.5 hours.

d) Preparation of $Me_2Si(2-Me-ind)_2Li_2$

The preparation was carried out as in step d) of example 1. The amounts used were: 12.0 g of dimethylsilylbis(2-methylindenyl), 44 g of toluene, 5.2 g of DME and 25.7 ml of BuLi solution. The suspension was heated to 60° C. and stirred for 1 hour, and subsequently cooled back down to room temperature.

e) Preparation of $Me_2Si(2\text{-Me-ind})_2Zr(2,4,6\text{-Me}_3\text{-C}_6H_2O)_2$ The suspension from step c) was transferred under nitrogen by means of a syringe into the suspension from step d) over a period of several minutes. The resulting suspension was stirred at room temperature for 2 hours. An $^1$H-NMR spectrum showed that the target compound had been formed in a rac/meso ratio of about 20:1. The suspension was filtered under nitrogen through a glass filter frit No. 3 into a round-bottom flask with stopcock and the filter cake was washed with 15 g of toluene. The filtrate was subsequently evaporated to about 60.8 g at 40° C. 71 g of heptane were added and the mixture was stirred for 15 minutes, resulting in crystallization of the complex.

The complex was filtered off and washed with 25 g of diisopropyl ether and dried under reduced pressure. This gave a total of 18.8 g (74%) of the target compound.

Elemental analysis:

|  | calculated: | found: |
| --- | --- | --- |
| C % | 71.06 | 69.9 |
| H % | 6.56 | 6.8 |

Example 5

Preparation of dimethylsilylbis(2-methylindenyl)zirconium bis(2,4,6-trimethylphenoxide) Starting from 2-methylindene in a Single-Vessel Process a) Preparation of $ZrCl_4(DME)_2$ The synthesis of this compound was carried out as described in example 4 a). The amounts used were 10.3 g (44.20 mmol) of $ZrCl_4$, 52.0 g of toluene, 4.9 g of DME.

b) Preparation of $Li(2,4,6\text{-Me}_3\text{-C}_6H_2O)$

The preparation of this compound was carried out as described in example 4 b). The amounts used were: 12.4 g (91.05 mmol) of 2,4,6-trimethylphenol, 48 g of toluene and 4.8 g of DME and also 28.4 g of a 20% strength by weight BuLi solution.

c) Preparation of $(DME)Cl_2Zr(2,4,6\text{-Me}_3\text{-C}_6H_2O)_2$

The preparation of this compound was carried out as described in example 4 c) using the above solutions b) and a). The resulting suspension was stirred for 0.5 hours.

d) Preparation of $Me_2Si(2\text{-Me-ind})_2Li_2$

In a dry three-neck round-bottom flask which had been flushed with inert gas and was provided with a dropping funnel and vacuum connection with stopcock, 10.9 g (79.71 mmol) of 2-methylindene were dissolved in 151 g of toluene and 8.3 g of DME. At room temperature, 26.8 g of a 20% strength by weight BuLi solution were slowly added dropwise over a period of 20 minutes. The resulting suspension was stirred at room temperature for 3 hours. 5.4 g of dichlorodimethylsilane were subsequently added dropwise and the dropping funnel was rinsed with 2 g of toluene. The mixture was heated to 45° C. and stirred at this temperature for a further 1.5 hours. After cooling to room temperature, a further 26.7 g of BuLi solution were added dropwise and the mixture was heated to 60° C. and stirred for 1.5 hours. The mixture was subsequently cooled and stirred at room temperature for 2 hours. GC and $^1$H-NMR analysis indicated 94% of the ligand.

e) Preparation of the Target Compound

The suspension from c) was transferred under nitrogen by means of a syringe into the suspension from step d) over a period of several minutes. The resulting solution was stirred at room temperature for 2 hours. The suspension was subsequently transferred under nitrogen by means of a syringe onto a glass filter frit Number 3 and filtered into a round-bottom flask with stopcock. The filter cake was washed twice with 10 g each time of toluene. A $^1$H-NMR spectrum of the filtrate showed the formation of the target compound in a rac:meso ratio of about 20:1. The filtrate was evaporated to about 80.6 g at 40° C. 70 g of heptane were subsequently added at room temperature, resulting in crystallization of the complex. The crystals were filtered off, washed with 28 g of diisopropyl ether and dried under reduced pressure. This gave a total of 13.8 g (51%) of the target compound.

Example 6

Preparation of dimethylsilylbis(2-methylindenyl)zirconium bis(2,6-dimethyl-4-bromophenoxide)

a) Preparation of $ZrCl_4(DME)$

The preparation of this compound was carried out as described in example 4 a). The amounts used were 5.70 g (24.46 mmol) of $ZrCl_4$, 70 ml of toluene and 2.20 g of DME.

b) Preparation of $Li(2,6\text{-Me}_2\text{-4-Br}—C_6H_2O)$

The preparation of this compound was carried out as described in example 4 b). The amounts used were 9.83 g (49.08 mmol) of 2,6-dimethyl-4-bromophenol, 70 ml of toluene, 4.40 g of DME and 20.0 ml of 20% strength by weight BuLi solution.

c) Preparation of $(DME)_xCl_2Zr(2,6\text{-Me}_2\text{-4-Br}—C_6H_2O)_2$

The preparation of this compound was carried out as described in example 4 c).

d) Preparation of $Me_2Si(2\text{-Me-ind})_2Li_2$

In a dry 1000 ml three-neck round-bottom flask which had been flushed with inert gas and was provided with a magnetic stirrer bar, dropping funnel and vacuum connection with stopcock, 7.74 g (24.45 mmol) of dimethylsilylbis(2-methylindenyl) were suspended in 100 ml of toluene and 15 ml of DME. At room temperature, 20.0 ml of a 20% strength by weight BuLi solution were slowly added dropwise over a period of 20 minutes. The mixture was subsequently heated to 60° C. and stirred for another one hour. The suspension was finally cooled to room temperature.

e) Preparation of $Me_2Si(2\text{-Me-ind})_2Zr(2,6\text{-Me}_2\text{-4-Br}—C_6H_2O)_2$ The suspension from step c) was transferred by means of a syringe into the suspension from step d) over a period of several minutes. The resulting suspension was heated to 40° C. and stirred at this temperature for 1 hour. An $^1$H-NMR spectrum showed the formation of the target compound in a rac:meso ratio of about 10:1. The suspension was heated to 60° C. and transferred while hot via a syringe to a glass filter frit number 4 and filtered into a round-bottom flask with stopcock. The filtrate was concentrated, with about 150 ml of the solvent being removed. The flask was stored at 0° C. for a number of days, resulting in formation of a precipitate.

The precipitate was isolated by filtration and drying under reduced pressure, giving a total of 9.49 g (48%) of the pure rac form of the target compound.

Elemental analysis:

|  | calculated: | found: |
| --- | --- | --- |
| C % | 56.7 | 56.5 |
| H % | 4.8 | 4.8 |

We claim:

1. A process for preparing racemic metallocene complexes of the formula (I)

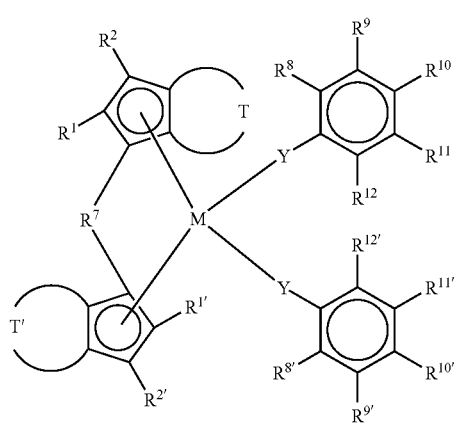

where

is a divalent group

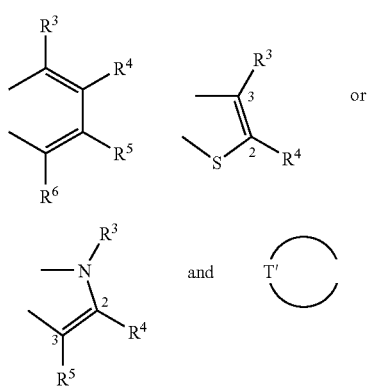

is a divalent group

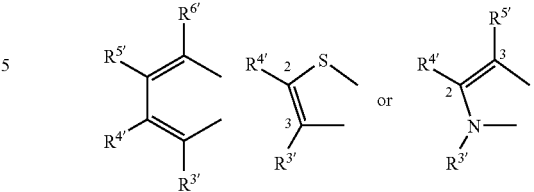

and the substituents and indices have the following meanings:

M is titanium, zirconium, hafnium, vanadium, niobium, tantalum, chromium, molybdenum or tungsten, $R^1, R^2, R^3, R^4, R^5, R^6, R^9, R^{10}, R^{11}, R^{1'}, R^{2'}, R^{3'}, R^{4'}, R^{5'}, R^{6'}, R^{9'}, R^{10'}$ and $R^{11'}$ are identical or different and are each hydrogen, halogen, $C_1$-$C_{20}$-alkyl, 3- to 8-membered cycloalkyl which optionally bears a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $-OR^{13}$, $-SR^{13}$, $-N(R^{13})_2$, $-P(R^{13})_2$, or $Si(R^{13})_3$, where $R^{13}$ are identical or different and are each $C_1$-$C_{10}$-alkyl, $C_6$-$C_{15}$-aryl, $C_3$-$C_{10}$-cycloalkyl, alkylaryl, where the radicals mentioned may be partially or fully substituted by heteroatoms, $R^8, R^{12}, R^{8'}$ and $R^{12'}$ are identical or different and are each $C_1$-$C_{10}$-alkyl, Y is oxygen $R^7$ is a -$[Z(R^{15})(R^{16})]_m$— group, where Z are identical or different and are each silicon, germanium, tin or carbon, $R^{15}$ and $R^{16}$ are each hydrogen, $C_1$-$C_{10}$-alkyl, $C_3$-$C_{10}$-cycloalkyl or $C_6$-$C_{15}$-aryl, m is 1, 2, 3 or 4, which comprises reacting a transition metal complex of the formula (II)

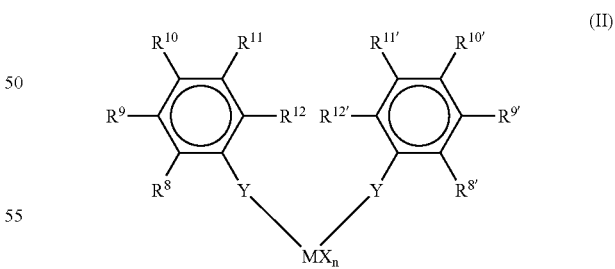

where

X are identical or different and are each hydrogen, halogen, $C_1$-$C_{10}$-alkyl, $C_6$-$C_{15}$-aryl, alkylaryl having from 1 to 10 carbon atoms in the alkyl part and from 6 to 20 carbon atoms in the aryl part, $-OR^{17}$ or $-NR^{17}_2$, where $R^{17}$ are identical or different and are each $C_1$-$C_{10}$-alkyl, $C_6$-$C_{15}$-aryl, $C_3$-$C_{10}$-cycloalkyl, alkylaryl, n is an integer from 1 to 4 and corresponds to the valence of M minus 2,
with cyclopentadienyl derivatives of the formula (III)

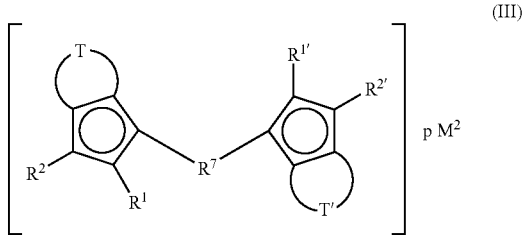

where
M² is an alkali metal ion or alkaline earth metal ion, and
p is 1 when M² is an alkaline earth metal ion and is 2 when M² is an alkali metal ion,
and heating the resulting reaction mixture to a temperature in the range from −78 to +250° C.

2. The process as claimed in claim 1,
wherein the substituents $R^8$, $R^{8'}$, $R^{12}$ and $R^{12'}$ are identical and are selected from the group consisting of methyl, ethyl, n-propyl, i-propyl, n-butyl, sec-butyl and tert-butyl.

3. The process as claimed in claim 1,
wherein the substituents $R^1$ and $R^{1'}$ are identical or different and are each hydrogen or methyl.

4. The process as claimed in claim 3,
wherein the substituents $R^8$, $R^{8'}$, $R^{12}$ and $R^{12'}$ are identical and are methyl.

5. The process as claimed in claim 1,
wherein M is titanium, zirconium or hafnium.

6. The process as claimed in claim 5,
wherein M is zirconium.

7. The process as claimed in claim 1,
wherein M² is magnesium or lithium.

8. The process as claimed in claim 1,
wherein $R^7$ is a dimethylsilyl group or an ethanediyl group.

9. The process as claimed in claim 1,
wherein in a further step, the compound of the formula (I) is reacted with suitable replacement reagents to replace at least one of the groups

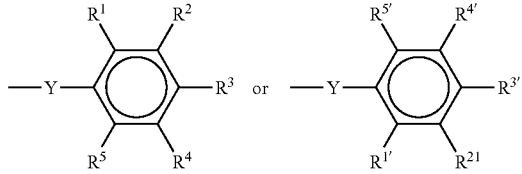

by halogen substituents F, Cl, Br or I or by linear, branched or cyclic $C_{1-10}$-alkyl substituents.

10. The process as claimed in claim 9,
wherein the replacement reagents are selected from the group consisting of aliphatic and aromatic carboxylic acid halides, organoaluminum compounds and combinations thereof.

11. The process as claimed in claim 9,
wherein the replacement reagents are selected from the group consisting of acetyl chloride, phenylacetyl chloride, 2-thiophenacetyl chloride, trichloroacetyl chloride, trimethylacetyl chloride, O-acetylmandelyl chloride, 1,3,5-benzenetricarboxylic chloride, 2,6-pyridinecarboxylic chloride, tert-butylacetyl chloride, chloroacetyl chloride, 4-chlorobenzacetyl chloride, dichloroacetyl chloride, 3-methoxyphenylacetyl chloride, acetyl bromide, bromoacetyl bromide, acetyl fluoride, benzoyl fluoride, $SOCl_2$, silicon tetrachloride, trimethylaluminum, triethylaluminum, tri-n-butylaluminum, triisobutylaluminum, and dialkylaluminum chlorides, aluminum sesquichlorides, methylaluminum dichloride, dimethylaluminum chloride, aluminum trichloride, ethylaluminum dichloride and combinations thereof.

12. The process as claimed in claim 10,
wherein replacement reagents used are HF, HBr, HI, or HCl, or as solutions in water, diethyl ether, DME or THF.

13. The process as claimed in claim 1,
wherein no intermediates are isolated during the process.

14. The process as claimed in claim 1 comprising the following steps:
a) deprotonating a compound of the formula (IV)

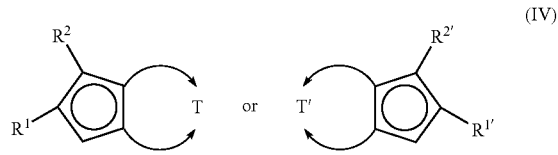

by means of a deprotonating agent;
b) reacting the deprotonated compound (IV) with a compound $R^7Hal_2$, where Hal is a halogen substituent F, Cl, Br or I, and subsequent repeat deprotonation by means of a suitable deprotonating agent to give the compound of the formula (III)

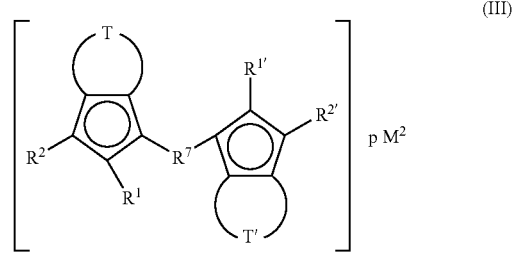

where
M² is an alkali metal ion or alkaline earth metal ion,
where
p is 1 when M² is an alkaline earth metal ion and is 2 when M² is an alkali metal ion, and $R^7$ is in claim 1;
c) reacting the compound of the formula (III) with a transition metal complex of the formula (II)

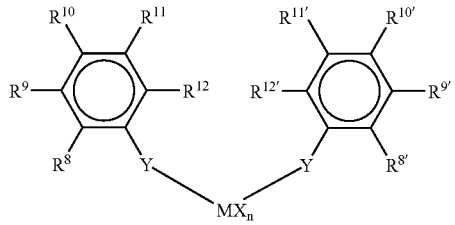

(II)

where

X are identical or different and are each hydrogen, halogen, $C_1$-$C_{10}$-alkyl, $C_6$-$C_{15}$-aryl, alkylaryl having from 1 to 10 carbon atoms in the alkyl part and from 6 to 20 carbon atoms in the aryl part, —$OR^{17}$ or —$NR^{17}_2$, where $R^{17}$ are identical or different and are each $C_1$-$C_{10}$-alkyl, $C_6$-$C_{15}$-aryl, $C_3$-$C_{10}$-cycloalkyl, alkylaryl, n is an integer from 1 to 4 and corresponds to the valence of M minus 2, and the other substituents in claim 1.

15. The process as claimed in claim 14, wherein the deprotonating agent is n-butyllithium, tert-butyllithium, sodium hydride, potassium tert-butoxide, or Grignard reagents of magnesium, magnesium compounds.

16. The process as claimed in claim 14, wherein the deprotonating agent is an alkaline earth metal alkyl or alkali metal alkyl compound.

17. A racemic metallocene complex of the formula (I)

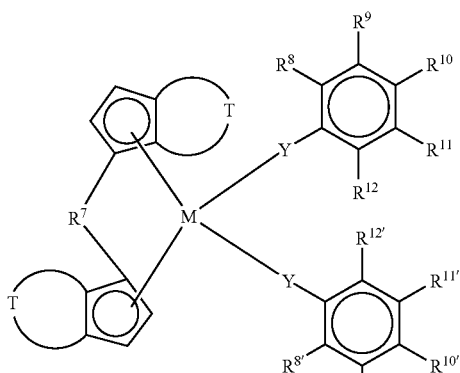

(I)

where

is a divalent group

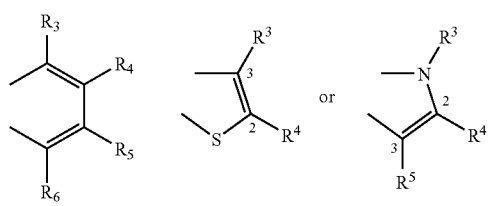

-continued and 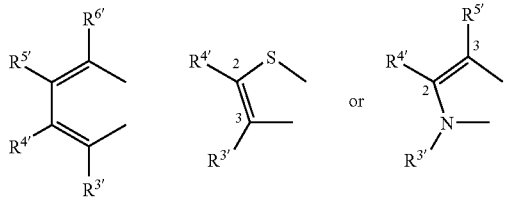

is a divalent group and the substituents and indices have the following meanings:

M is titanium, zirconium hafnium, vanadium, niobium, tantalum, chromium, molybdenum or tungsten, $R^1$, $R^2$, $R^3$, $R^4$, $R^5$, $R^6$, $R^9$, $R^{10}$, $R^{11}$, $R^{1'}$, $R^{2'}$, $R^{3'}$, $R^{4'}$, $R^{5'}$, $R^{6'}$, $R^{9'}$, $R^{10'}$, and $R^{11'}$ are identical or different and are each hydrogen, halogen, $C_1$-$C_{20}$-alkyl, 3- to 8-membered cycloalkyl which optionally bears a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, —$OR^{13}$, —$SR^{13}$, —$N(R^{13})_2$, —$P(R^{13})_2$ or $Si(R^{13})_3$, where $R^{13}$ are identical or different and are each $C_1$-$C_{10}$-alkyl, $C_6$-$C_{15}$-aryl, $C_3$-$C_{10}$-cycloalkyl, alkylaryl, where the radicals mentioned may be partially or fully substituted by heteroatoms, $R^8$, $R^{12}$, $R^{8'}$ and $R^{12'}$ are identical or different and are each $C_1$-$C_{10}$-alkyl, Y are oxygen $R^7$ is a -[$Z(R^{15})(R^{16})]_m$— group, where Z are identical or different and are each silicon, germanium, tin or carbon, $R^{15}$ and $R^{16}$ are each hydrogen, $C_1$-$C_{10}$-alkyl, $C_3$-$C_{10}$-cycloalkyl or $C_6$-$C_{15}$-aryl, and m is 1, 2, 3 or 4.

18. The complex as claimed in claim 17 selected from the group consisting of dimethylsilylbis(1-indenyl)zirconium bis(2,4,6-trimethylphenoxide), dimethylsilylbis(2-methyl-1-indenyl)zirconium bis(2,4,6-trimethylphenoxide), dimethylsilylbis(2-methyl-1-indenyl)zirconium bis(2,6-dimethylphenoxide), dimethylsilylbis(2-methyl-1-indenyl)zirconium bis(2,6-dimethyl-4-bromophenoxide) and ethanediylbis(1-indenyl)zirconium bis(2,4,6-trimethylphenoxide).

19. The complex as claimed in claim 17,
wherein the substituents $R^8$, $R^{8'}$, $R^{12}$ and $R^{12'}$ are identical and are selected from the group consisting of methyl, ethyl, n-propyl, i-propyl, n-butyl, sec-butyl and tert-butyl.

20. The complex as claimed in claim 17,
wherein the substituents $R^1$ and $R^{1'}$ are identical or different and are each hydrogen or methyl.

21. The complex as claimed in claim 20,
wherein the substituents $R^8$, $R^{8'}$, $R^{12}$ and $R^{12'}$ are identical and are methyl.

22. The complex as claimed in claim 17, wherein M is titanium, zirconium or hafnium.

23. The complex as claimed in claim 22, wherein M is zirconium.

24. The complex as claimed in claim 1, wherein $M^2$ is magnesium or lithium.

25. The complex as claimed in claim 17, wherein $R^7$ is a dimethylsilyl group or an ethanediyl group.

26. A catalyst comprising the racemic metallocene complex of claim 17.

27. A process for polymerizing olefinically unsaturated compounds which comprises using the catalyst as claimed in claim 26.

28. A process for stereoselective synthesis which comprises using the catalyst as claimed in claim 26.

* * * * *